United States Patent [19]
Tischer et al.

[11] Patent Number: 4,950,609
[45] Date of Patent: Aug. 21, 1990

[54] STABILIZED SARCOSINE OXIDASE PREPARATION

[75] Inventors: Wilhelm Tischer, Peissenberg; Manfred Gloger, Weilheim; Josef Heinle, München, all of Fed. Rep. of Germany

[73] Assignee: Boehringer Mannheim GMBH, Mannheim, Fed. Rep. of Germany

[21] Appl. No.: 844,691

[22] Filed: Mar. 27, 1986

[30] Foreign Application Priority Data

Apr. 30, 1985 [DE] Fed. Rep. of Germany ....... 3515586

[51] Int. Cl.$^5$ .......................... C12Q 1/00; C12Q 1/34; C12Q 1/26; C12N 11/16
[52] U.S. Cl. ......................................... 435/18; 435/4; 435/25; 435/174; 435/175; 435/178; 435/188; 435/227; 435/228; 435/810
[58] Field of Search ....................... 435/4, 25, 18, 174, 435/175, 178, 810, 188, 227, 228

[56] References Cited

U.S. PATENT DOCUMENTS 3,944,470  3/1976  Diehl et al. ........................ 435/188
4,460,683  7/1984  Gloger et al. ........................ 435/10
4,665,023  5/1987  Deneke et al. ........................ 435/28

FOREIGN PATENT DOCUMENTS 7900609  8/1979  PCT Int'l Appl. .

OTHER PUBLICATIONS

Clinical Chemistry, Band 29, Nr. 1, Jan. 1983, Seiten 51–55; "Multi-Enzyme Membrane Electrodes for determination of Creatinine and Creatin Serum".
Chem. Abstracts, Band 93, Nr. 7, Aug. 1980, Seite 735, Nr. 68681, Columbus, Ohio.
Chem. Abstracts, Band 97, Nr. 5, Aug. 1982, Seite 249, Nr. 35365c, Columbus, Ohio.

Primary Examiner—Esther M. Kepplinger
Assistant Examiner—Janelle Graeter
Attorney, Agent, or Firm—Felfe & Lynch

[57] ABSTRACT

The present invention provides a stabilized sarcosine oxidase preparation which contains creatineamidinohydrolase covalently bound to a water-soluble polysaccharide.

14 Claims, 1 Drawing Sheet

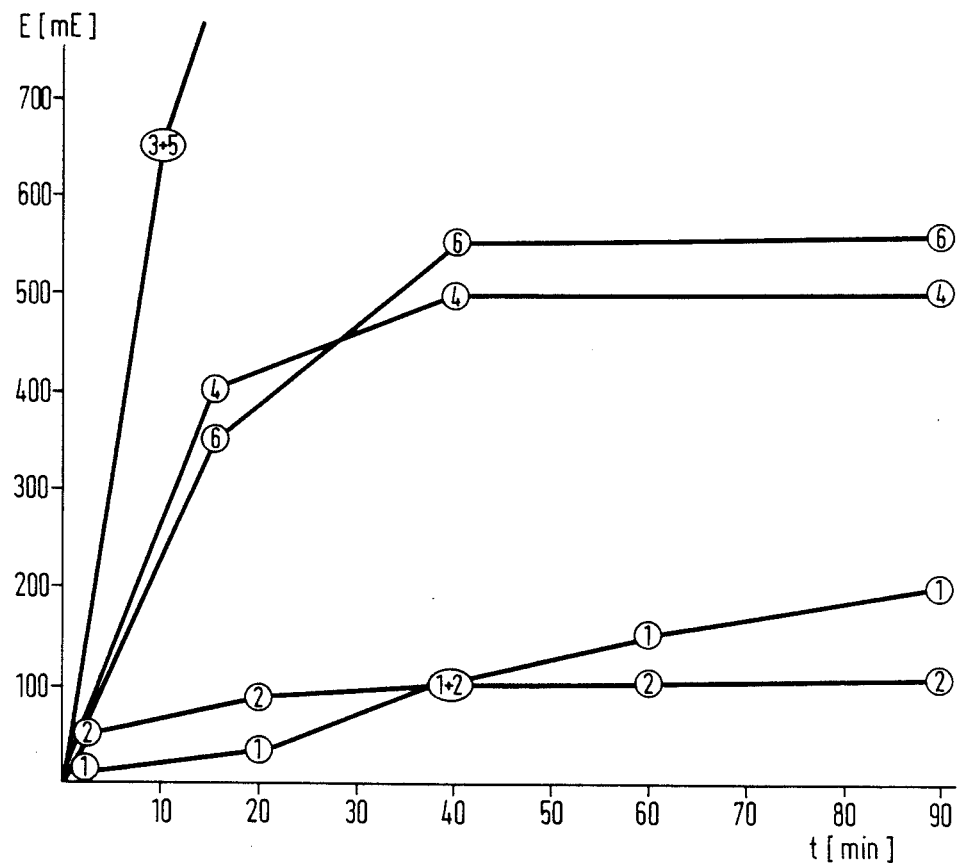

STABILIZED SARCOSINE OXIDASE PREPARATION

The present invention is concerned with a stabilised sarcosine oxidase preparation and with the use thereof.

Sarcosine oxidase (E.C. 1.5.3.1) (Sarco-OD) catalyses the reaction of sarcosine with oxygen and water with the formation of formaldehyde and hydrogen peroxide. On the basis of this reaction, in which the hydrogen peroxide can easily be removed from the equilibrium, it can be used for the determination of sarcosine. Sarcosine in turn is formed by the hydrolysis of creatine by the action of the enzyme creatineamidinohydrolase (E.C. 3.5.3.3), whereby, with the take up of water, sarcosine and urea are formed. Since, finally, creatine is formed from creatinine enzymatically, the determination of sarcosine in the above-described manner also makes possible a determination of creatine and of creatinine. The determination of creatinine in blood serum is of considerable clinical importance.

However, in order to be able to use sarcosine oxidase in a reagent for the determination of sarcosine, creatine or creatinine, it is, in practice, of decisive importance that the enzyme-las a sufficient stability in dried (lyophilised) form and especially in reconstituted, dissolved form. The absence of this property has hitherto prevented the practical use of sarcosine oxidase in the described manner for the determination of sarcosine. Thus, sarcosine oxidase in buffered aqueous solution shows a distinct turbidity after only a few hours which must be taken into account, especially in the case of optical methods of measurement. The minimum period of stability of a few days, which is necessary for a commercially usable reagent, is not achieved.

Therefore, it is an object of the present invention to provide a stabilized sarcosine oxidase preparation which does not display the above-mentioned disadvantages ahd can be used for a commercial determination of sarcosihe.

Thus, according to the present invention, there is provided a stabilized sarcosine oxidase preparation which contains creatineamidinohydrolase covalently bound to a water-soluble polysaccharide.

Surprisingly, the polysaccharide-bound creatineamidinohydrolase prevents turbidity formation by sarcosine oxidase. The reason for this effect is not known. It appears to be possible that the two enzymes combine in the manner of a complex since one of the enzymes gives sarcosine as a product which is taken up directly by the other enzyme as substrate, whereby the carbohydrate part of,the one enzyme could then protect the other enzyme against unstabilising influences.

Thus, if the three components of this preparation, without covalent binding between the polysaccharide and the creatineamidinohydrolase, are mixed together, then turbidity formation cannot be prevented.

Polysaccharides which can be used according to the present invention include soluble starch, glycogen, dextran, inulin, pectin, mannan and galactan, dextran being preferred.

An especial advantage of the stabilized enzyme preparation according to the present invention is the fact that, even in the presence of surface-active agents, which, as a rule, rapidly make turbid nonstabilized sarcosine oxidase, it has an improved stability. Since, as a rule, surface-active agents are needed when metabolic products, such as sarcosine, are to be determined in body fluids, especially in serum, in order to prevent a turbidity formation by other serum components, this is an important advantage of the preparation according to the present invention. Therefore, the preparation preferably also contains at least one surface-active agent. As surface-active agents, there are hereby especially preferred the substances known as components of so-called "clarification systems" for serum. Typical examples therefor include non-ionic surface-active substances and anionic surface-active substances, especially of the cholic acid group.

The covalent binding of the creatineamidinohydrolase to the polysaccharide for the production of the stabilizer used according to the present invention (polysaccharide-enzyme conjugate) can take place according to the known methods for the carrier fixing of enzymes. In the case of the use of dextran as polysaccharide, binding via cyanogen bromide or trichlorotriazine (TCT) has proved to be especially suitable, the coupling agent preferably first being reacted with the dextran with the formation of a corresponding activated dextran which then binds the creatineamidinohydrolase covalently in aqueous solution. Polysaccharide and enzyme are preferably used in a weight ratio of from 1:1 to 20 and preferably of from 1:4 to 15.

Because of its superior stability, the sarcosine oxidase preparation according to the present invention can even be mixed together with a system for the determination of hydrogen peroxide formed by the sarcosine oxidase, as well as with buffer and, if the preparation is to be used in the scope of a creatinine determination, creatininamidohydrolase can also be added thereto without the stability hereby being reduced.

As buffer in the scope of the present invention, there can be used all buffer substances which buffer in the scope of the known stability range of Sarc-0D and of creatineamidinohydrolase. Preferred examples of buffers which can be used include phosphate buffer and tris buffer. The preferred pH range is from 7.0 to 8.5 and especially from 7.6 to 8.2. Appropriate concentrations are,for example, from 50 to 500 mmol/l.

As systems for the determination of hydrogen peroxide, there can be used those known for this purpose which do not contain any components which impair the activity of the enzymes. Typical examples for such systems are described in H. U. Bergmeyer's "Methoden der enzymatischen Analyse", 4th edition. The clarification system can consist, for example, of a non-ionic surface-active agent, such as n-decanol polyglycol ether (Lutensol ON 50), optionally together with an anionic surface-active agent of the cholic acid group, such as sodium cholate, and a halogenated phenol, such as 2,4,6-tribromo-3-hydroxybenzoic acid. Finally, the preparation can also be admixed with conventional preserving agents, for example alkali metal azides.

According to a further preferred embodiment of the present invention, the sarcosine oxidase can be present in the preparation according to the present invention in a pre-cross-linked form. Such a pre-crosslinked sarcosine oxidase can be obtained by reaction with bifunctional protein reagents, such as are described, for example, in Federal Republic of Germany Patent Specifications Nos. 21 28 743 and 22 60 185, a sarcosine oxidase pre-cross-linked with glutardialdehyde being especially preferred. A further improvement of the stability of the sarcosine oxidase preparation according to the present invention can hereby be achieved.

BRIEF DESCRIPTION OF THE DRAWING

The single figure shows a plot of the extinction measured at 546 mm versus incubation time using a number of sarcosine oxidase preparations.

The stabilizing effect achieved by means of the present invention in the absence or presence of surfaceactive agents can be seen from the accompanying drawing. In this, the turbidity formation measured as extinction at 546 nm is plotted against the incubation time of the sarcosine oxidase in minutes at 37° C. In all cases, there is used native sarcosine oxidase in 300 mM phosphate buffer (pH 7.9). Curve 1 is for Sarc-OD, curve 2 is for Sarc-OD + dextran-enzyme conjugate, curve 3 corresponds to curve 1 with the addition of 0.1% Lutensol (surface-active agent), curve 4 corresponds to curve 3 with the addition of dextran-enzyme conjugate, curve 5 corresponds to curve 3 with the addition of 0.4% Lutensol and curve 6 corresponds to curve 5 with the addition of dextran-enzyme conjugate. The amount of dextran-enzyme conjugate is thereby, in all cases, 12 U/ml., the amount of sarcosine oxidase is 6.5 U/ml. and the concentration of creatineamidinohydrolase is 12 U/ml. The ratio of enzyme:dextran in the conjugate is 1:4.

As can be seen from the curves, within 90 minutes at the given temperature, there is a turbidity with native sarcosine oxidase which is already about twice as great as in the presence of the dextran-enzyme conjugate as stabiliser. In the presence of surface-active agents, the turbidity without the stabilizer is so strong that after 15 minutes the limits of measurement is already exceeded. On the other hand, in the presence of surface-active agents and stabilizer, a turbidity admittedly occurs initially but remains within the measurement range and after about 40 minutes does not increase further. Thus, the present invention makes it possible to obtain reagents of sufficiently long stability for the determination of sarcosine, creatine or creatinine and thus to bring the sarcosine determination by means of sarcosine oxidase and, beyond this, also the determination of creatine and creatinine into a practically usable form.

The following Examples are given for the purpose of illustrating the present invention:

EXAMPLE 1.

Preparation of the stabilizer.

Soluble dextrans (Roth, Karlsruhe) with average molecular weights of 10,000; 20,000; 40,000 and 500,000 are reacted with cyanogen bromide at pH 10.6.

For this purpose, 120 g. of dextran are dissolved in 12 liters water and adjusted to pH 10.6 with 2N aqueous sodium hydroxide solution. While stirring, a total of 36 to 60 g. cyanogen bromide are added thereto in 12 g. portions to the reaction mixture in the course of 40 minutes. The pH value is hereby maintained at 10.6 by the addition of 2N aqueous sodium hydroxide solution. The activation reaction is finished when no more aqueous sodium hydroxide solution is consumed.

The clear solution obtained is adjusted to pH 8.0 with 2 mole/litre hydrochloric acid and the activated dextran obtained is dialysed against water for 2 hours at 20° C.

44.4 g. Commercially available creatineamidinohydrolase in lyophilised form (4.2 U/mg.; 0.54 mg. protein/mg. lyophilisate), corresponding to about 24 g. enzyme protein, are dissolved in 250 ml. 20 mmol/litre phosphate buffer (pH 8.0) and dialysed against 20 litres of the same buffer. The enzyme solution thus obtained is combined with the activated dextran solution prepared as described above and slowly stirred for 16 hours at ambient temperature. The dextran-enzyme conjugate obtained is dialysed for 3 hours against 0.04 mole/litre sodium citrate buffer (pH 5.8). 24 g. raffinose are then added thereto and the solution is clarified by filtration and lyophilised. 80% of the enzyme activity used is present in the lyophilisate.

EXAMPLE 2.

By mixing together the reagents, there is produced a stabilized sarcosine oxidase preparation which is suitable as a reagent for the determination of creatinine and, as an aqueous solution, has the following composition:

6.5 U/ml. sarcosine oxidase,
12 U/ml. creatineamidinohydrolase-dextran conjugate,
25 U/ml. creatineamidohydrolase,
2 U/ml. peroxidase,
2 U/ml. cholesterol esterase from Candida cylindracea,
150 50 mmol/l. potassium phosphate buffer (pH 7.9),
0.3% Lutensol ON 50,
8.6 mmol/liter 2,4,6-tribromo-3-hydroxybenzoic acid,
5 mmole/litre sodium cholate,
0.5 mmol/l Titriplex III,
0.2% sodium azide,
10 μmole/liter potassium ferrocyanide.

The above reagent is lyophilised. After reconstitution with water, there is obtained a solution which remains usable for at least 2 days for the optical determination of creatinine.

We claim:

1. A stabilized sarcosine oxidase preparation for determination of creatinine comprising sarcosine oxidase and creatinineamidahydrolase together with creatine amidinohydrolase which is covalently bound to a water-soluble polysaccharide.

2. The sarcosine oxidase preparation of claim 1, wherein the water-soluble polysaccharide is a soluble starch, glycogen, dextran, inulin, pectin, mannan or galactan.

3. The sarcosine oxidase preparation of claim 2, further comprising a surface-active agent.

4. The sarcosine oxidase preparation of claim 1 wherein the creatineamidinohydrolase is bound to dextran activated with cyanogen bromide or trichlorotriazine.

5. The sarcosine oxidase preparation of claim 1 further comprising, buffer and a system for the determination of hydrogen peroxide.

6. The sarcosine preparation of claim 1 further comprising an anionic or non-ionic surface-active agent.

7. The sarcosine oxidase preparation of claim 1 wherein the sarcosine oxidase is crosslinked sarcosine oxidase.

8. The sarcosine oxidase preparation of claim 1 wherein the sarcosine oxidase is crosslinked with glutardialdehyde.

9. A stabilized sarcosine oxidase preparation for the determination of creatinine comprising sarcosine oxidase, creatinineamidohydrolase and creatine amidinohydrolase which is covalently bound to a soluble starch, glycogen, dextran, inulin, pectin, mannan or galactan; and a system for determination of hydrogen peroxide.

10. The sarcosine oxidase preparation of claim 9 further comprising a buffer in the pH range 7.0 to 8.5.

11. The sarcosine preparation of claim 10 wherein said buffer is a phosphate or tris buffer.

12. In a method for determining creatinine by using the enzymes sarcosine oxidase, creatineamidinohydrolase and creatinineamidohydrolase, and measuring the hydrogen peroxide produced as a measure of creatinine present in the sample, the improvement comprising adding the creatineamidinohydrolase covalently bound to a water-soluble polysaccharide as a a stabilized.

13. In the method of claim 12, the improvement further comprising adding a crosslinked sarcosine oxidase.

14. In the method of claim 13, the improvement further comprising adding a sarcosine oxidase crosslinked with glutardialdehyde.

* * * * *

UNITED STATES PATENT AND TRADEMARK OFFICE
CERTIFICATE OF CORRECTION

PATENT NO. : 4,950,609

DATED : August 21, 1990

INVENTOR(S) : Wilhelm Tischer, et al

It is certified that error appears in the above-identified patent and that said Letters Patent is hereby corrected as shown below:

The sheet of drawing consisting of Fig. 1 should be added as shown on the attached sheet.

Signed and Sealed this

Twentieth Day of October, 1992

Attest:

DOUGLAS B. COMER

Attesting Officer

Acting Commissioner of Patents and Trademarks

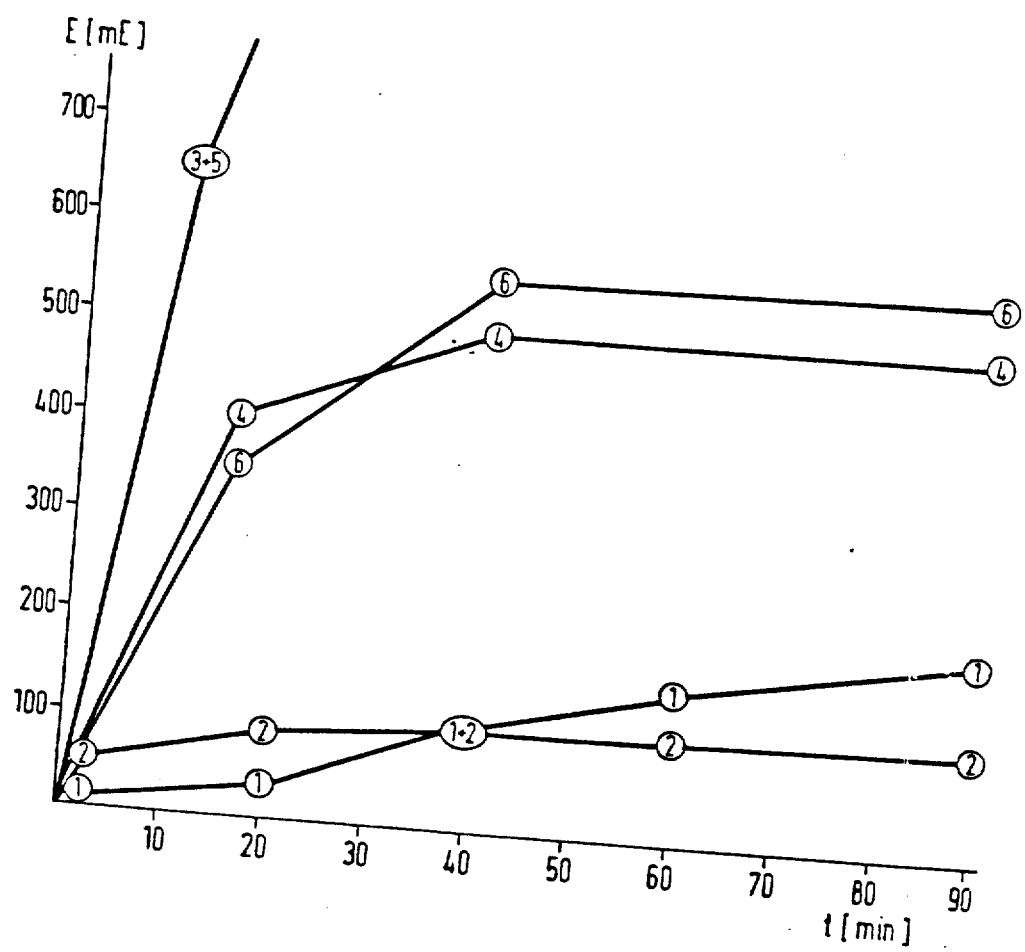

UNITED STATES PATENT AND TRADEMARK OFFICE
CERTIFICATE OF CORRECTION

PATENT NO.  : 4,950,609
DATED       : August 21, 1990
INVENTOR(S) : Wilhelm Tischer, et al.

It is certified that error appears in the above-identified patent and that said Letters Patent is hereby corrected as shown below:

Col. 1, line 25:        change "enzyme-las" to -- enzyme has --.

Col. 1, line 39:        change "ahd" to -- and --.

Col. 1, line 40:        change "sarcosihe" to -- sarcosine --.

Col. 4, line 24:        change "150 50 mmole/1." to
                        -- 150 mmol/l. --.

Col. 4, line 39
   Claim 1:             change "creatinineamidahydrolase" to
                        -- creatinineamidohydrolase --.

Col. 4, line 53
   Claim 5:             after "comprising" insert
                        -- creatineamidinohydrolase, --.

Col. 6, line 3
   Claim 12:            delete "a" third occurrence and after
                        "stabilized" insert -- preparation --.

Signed and Sealed this

Ninth Day of February, 1993

Attest:

STEPHEN G. KUNIN

*Attesting Officer*            Acting Commissioner of Patents and Trademarks